United States Patent [19]

Dreyfuss et al.

[11] 4,173,629

[45] Nov. 6, 1979

[54] ANTIBIOTIC S 31794/F-1

[75] Inventors: Michael M. Dreyfuss, Basel; Hans Tscherter, Allschwil, both of Switzerland

[73] Assignee: Sandoz Ltd., Basel, Switzerland

[21] Appl. No.: 919,760

[22] Filed: Jun. 28, 1978

Related U.S. Application Data

[63] Continuation of Ser. No. 702,210, Jul. 2, 1976, abandoned.

[30] Foreign Application Priority Data

Jul. 8, 1975 [CH]  Switzerland ..................... 8894/75

[51] Int. Cl.² ............................................. A61K 35/00

[52] U.S. Cl. ................................. 424/118; 424/119; 435/171

[58] Field of Search .................. 424/118, 119; 195/81

[56] References Cited

U.S. PATENT DOCUMENTS 3,843,784  10/1974  Hamill et al. ........................ 424/119

Primary Examiner—Jerome D. Goldberg
Attorney, Agent, or Firm—Gerald D. Sharkin; Robert S. Honor; Timothy G. Rothwell

[57] ABSTRACT

This invention provides S 31794/F-1 which is a useful anti-mycotic for combatting *Candida albicans* infections.

6 Claims, 4 Drawing Figures

ANTIBIOTIC S 31794/F-1

This is a continuation, of application Ser. No. 702,210 filed July 2, 1976 which is now abandoned.

The present invention relates to the compound S 31794/F-1, as hereinafter defined.

The present invention provides a process for producing S 31794/F-1, which comprises cultivating a S 31794/F-1 producing strain of the fungus species *Acrophialophora limonispora* nov. spec. Dreyfuss + Muller in the presence of nutrient medium.

The compound S 31794/F-1 exhibits the following characteristics:

White amorphous powder, which may be obtained in crystalline form as described in the Example 3 hereinafter. All following data relate to both the crystalline and amorphous forms unless otherwise indicated.

M.Pt. 178°–180° C. (decomp.) [amorphous]
M.Pt. 181°–183° C. (decomp.) [crystalline]
$[\alpha]_D^{20} = -24°$ (c=0.5 in methanol)
$[\alpha]_D^{20} = +37°$ (c=0.5 in methanol) [crystalline]
UV [CH$_3$OH] see FIG. 1—$\lambda_{MAX}$ 194 nm $E_1\,cm^{1\%}=807$; $\lambda_{MAX}$ 225 nm (Shoulder) $E_1\,cm^{1\%}$ 132 $\lambda_{MAX}$ 276 nm $E_1\,cm^{1\%}$ 12.8 $\lambda_{MAX}$ 284 nm (Shoulder) $E_1\,cm^{1\%}$ 10.5

Figure 2:
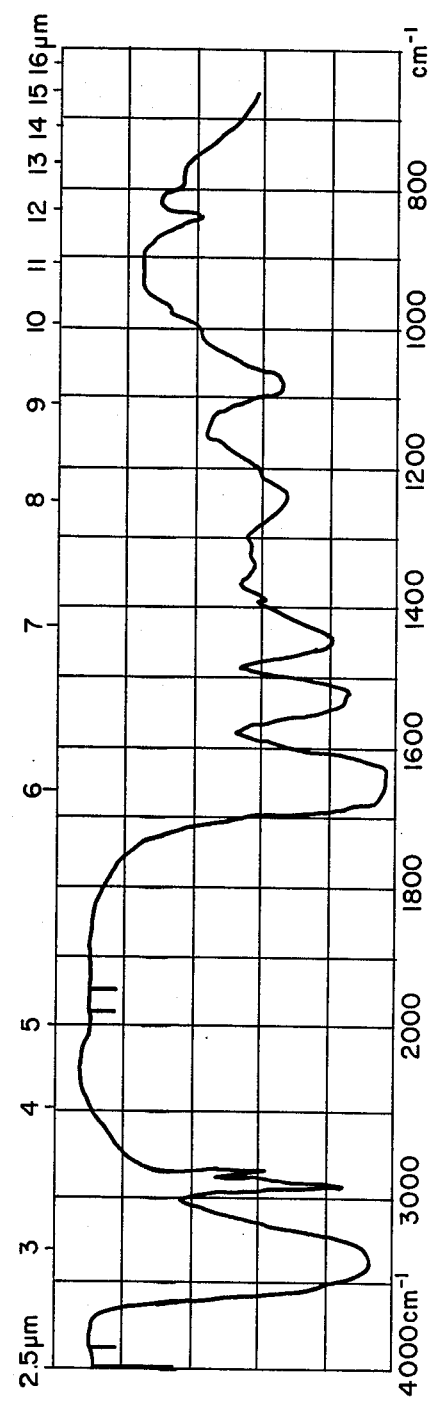
Figure 3:
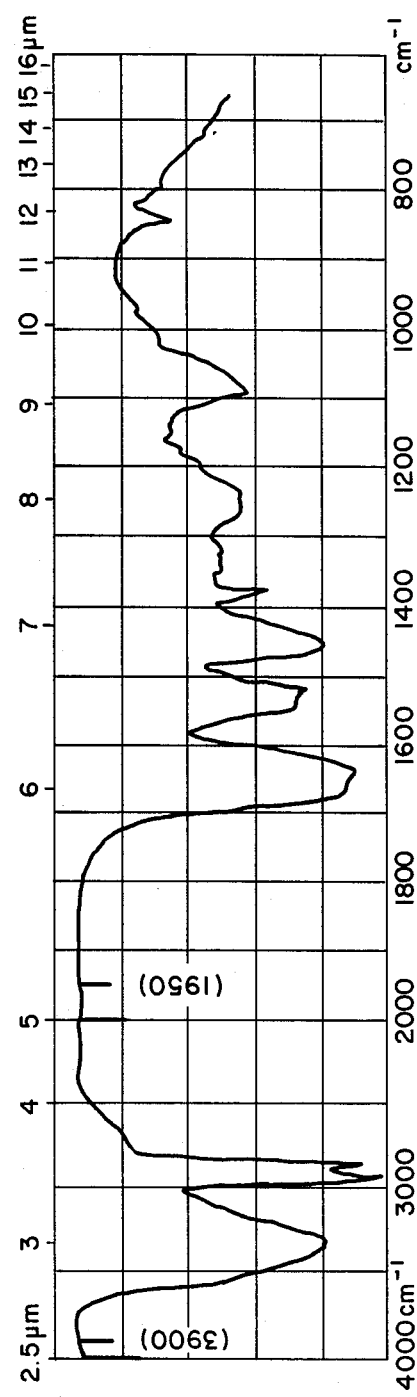

IR spectrum for amorphous form [in KBr] see FIG. 2
IR spectrum for crystalline form [in Nujol] see FIG. 3

Figure 4:
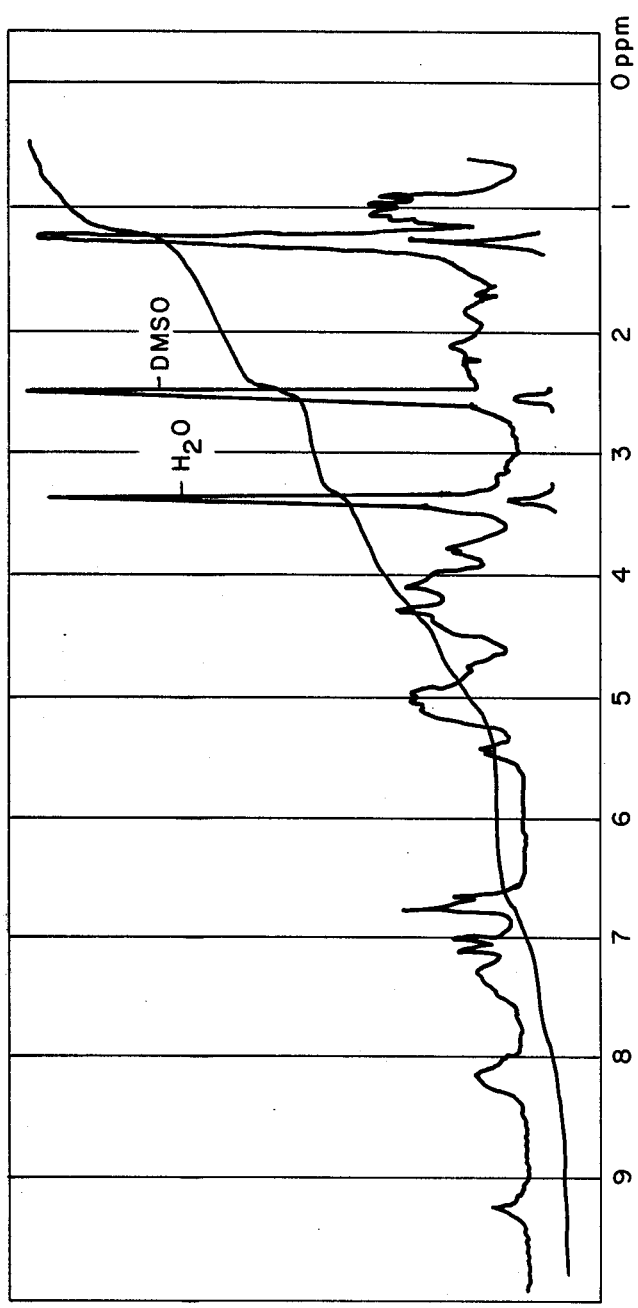

$^1$H—n.m.r. spectrum (100 MHz in deuterated DMSO) with tetramethylsilane as internal standard.—see FIG. 4

$^{13}$C—n.m.r. spectrum of 190 mg of S 31794/F-1 in 1.5 ml deuterated methanol (D$_4$) with tetramethylsilane as internal standard (=0 ppm)—see Table 1.

Apparatus Bruker HX-90-E; 22.63 MH$_2$. Sweep width 6000 Hz S 31794/F-1 is used in crystalline form.

Table 1

| PPM | PPM | PPM |
|---|---|---|
| 176.2 | 75.5 | 51.2 |
| 175.0 | 74.0 | 39.7 |
| 173.7 | 71.0 | 38.8 |
| 172.6 | 70.5 | 36.6 |
| 172.0 | 69.7 | 34.8 |
| 171.8 | 68.0 | 32.8 |
| 171.7 | 62.2 | 30.6 |
| 168.6 | 58.3 | 26.7 |
| 157.7 | 57.0 | 23.5 |
| 132.5 | 56.2 | 19.7 |
| 129.0 | 55.4 | 14.3 |
| 115.9 | 52.9 | 11.1 |
| 76.6 | | |

Analysis

The amorphous substance was dried at 20° C. in a high vacuum and gave the following values:
C. 53.9%; H. 7.5%; N. 10.1%; O. 27.3%.

The crystalline substance was dried at 100° C. for 2 hours at 100° C. in a high vacuum and lay within the following limits:
C. 55.5–56.5%; H. 7.5–7.7%; N. 10.5–10.8%; O. 26.5–27.0%.

Solubility

S 31794/F-1 is easily soluble in methanol, ethanol, pyridine and dimethyl sulphoxide, and difficulty soluble in water, chloroform, ethyl acetate, diethyl ether, benzene and hexane.

Stability

S 31794/F-1 is stable in aqueous methanol at pH 3–7.5. In alkaline or strong acidic conditions the compound decomposes, losing its anti-fungal activity.

Hydrolysis

By acid hydrolysis (6 NHCl at 110° C.) myristrinic acid was identified as a hydrolysis product and was identified in the form of its methyl ester.

Thin layer chromatography

Silica gel (Merck; Registered Trade Mark) plates with a layer 0.25 mm thick were used. The plates may be developed using iodine or other conventional means, e.g. by spraying a mixture of 0.5% acetic acid in ethanol + acetone (1:1), maintaining the plates in a chlorine atmosphere for ca. 7 minutes, removing excess chlorine by an air stream, and finally spraying with a mixture of 1 part 0.05 molar aqueous potassium iodide and 4 parts of a 1% benzidine solution in 20% aqueous acetic acid. The compound S 31794/F-1 shows as a blue spot.

| Eluant | Rf S 31794/F-1 |
|---|---|
| CHCl$_3$:CH$_3$OH:H$_2$O (71:25:4) | 0.17 (0.4)* |
| CHCl$_3$:CH$_3$OH:H$_3$COOH (70:29:1) | 0.19 (0.6)* |
| CHCl$_3$:CH$_3$OH (2:1) | 0.27 (0.5)* |

*= corresponding Rf values of Uracil given in parentheses.

With Ninhydrin there is no colouration.

The process according to the invention may be effected in conventional manner for the cultivation of analogous strains, e.g. as described in the following Examples.

A preferred culture strain for the production of S 31794/F-1 has been deposited at the United States Department of Agriculture (Northern Utilization Research and Development Division) Peoria, Ill., U.S.A. under the code NRRL 8095 and is freely available from the depository or the patentees.

Instead of the strain NRRL 8095, other strains derived from the original strain of the fungus species *Acrophialophoria limonispora* nov. spec. Dreyfuss + Muller by treatment with mutagenic agents or rays or by selection may used.

Characteristics of strain NRRL 8095

The new strain NRRL 8095 was originally isolated from a soil sample collected in British Columbia, Canada. On the basis of its morphological characteristics the strain appears to belong to the hyphomyete genus Acrophialophora Edward, but it differs from the three previously described species of this genus (see Samson and Tariq Mahmood, 1970: The Genus Acrophialophora in Acta bot. Neerl. 19 (6); 804–808), so the new strain has been designated as a new species, *Acrophialophora limonispora* nov. spec.

The light to deep brown conidiophores of *Acrophialophora limonispora* NRRL 8095 generally are 700 to 1800μ long and 4μ to 8μ thick, septated, straight or slightly bent. In their basal and middle parts they are unbranched or branched a few times and may be sculptured with warts over the whole length. At the tip of the conidiophore a symmetric or asymmetric, generally compact, penicillus-like branched system develops by branching at the terminal cells of the conidiophore main axis; the primary branches may be one- or few-celled, and develop singly, or in two or three (rarely four) units opposite to each other. These side branches carry laterally and apically several secondary branches, which may be analogously tertiary branched. On the secondary or tertiary branches emerge flask-shaped phialides which elongate to a narrow neck and which are 7–11×2.5–4μ in size. Especially in old cultures penicilles may be observed which contain very elongated branching elements.

The hyaline conida which are formed in basipetal, easily disintegrating chains are, when viewed from the side, broadly lemon-shaped with darker-appearing small apiculi, 3.2–4.2×3.0–3.5μ in size, and on the surface smooth or slightly verrucose.

The strain NRRL 8095 has a very wide growth optimum from 20° to 27° C., colonies attaining a diameter of 35 to 40 mm after seven days growth on 2% malt agar. The lower temperature limit for growth lies at 4° C., and the upper limit between 33° and 34° C.

Colonies on 2% malt extract agar are initially greenish-white and are covered with a very loose, white aerial mycelium. With increasing age the substrate mycelium becomes dark brown. In the course of 5 to 10 days the originally formed aerial mycelium becomes gradually overgrown by the conidiophores which develop in a dense lawn which initially appears golden-yellow to yellowish-green and later turns light to deep—to grey-brown.

The new strain may be cultured in the usual nutrient media using surface or submersed cultures. Preferably submersed cultures are used in appropriate nutrient media, for example as described in Example 1 and 2, which are inoculated with a conidia- or mycelium-suspension of the strain NRRL 8095. The cultures are incubated at a pH of from 3 to 8, preferably 5–7.0, at a temperature of from 15° to 30°, preferably 18°–27° with stirring, shaking, and/or aeration for 48 to 360 hours, preferably from 120 to 288 hours.

The mycelium part of the culture broth may be optionally broken down, and S 31794/F-1 may be obtained therefrom by the usual extraction and/or adsorption methods. If desired the mycelium may be centrifuged off from the culture broth and the mycelium and culture broth may be separately extracted. The two extracts may be worked up in conventional manner either separately or together.

The present invention also provides culture broths obtained by cultivating a S 31794/F-1 producing strain in a nutrient medium.

The compound S 31794/F-1 exhibits interesting activity. In particular the compound may be characterized biologically by its activity spectrum. It does not exhibit a significant effect against the usual gram-positive and gram-negative bacteria. It exhibits, however, a pronounced effect against yeast and fungi, particularly against Candida strains as indicated in the following Table:

| Strain | MIC (μg/ml) |
| --- | --- |
| Candida albicans | 0.3 |
| Candida krusei | 1 |
| Candida tropicalis | 0.3 |
| Candida albicans 5897 | 0.3 |

| Strain | MIC (μg/ml) |
| --- | --- |
| Candida albicans H 12 | 0.3 |
| Candida albicans Blast. res. | 0.03 |
| Candida tropicalis CK 4 | 0.01 |
| Candida albicans 439 | 0.03 |
| Trichophyton mentagrophytes | 32 |
| Trichophyton quinckeanum | >100 |
| Blastomyces dermatitidis | 100 |
| Sporotrichum schenkii | >100 |
| Aspergillus niger | 100 |
| Aspergillus fumigatus | 32 |
| Microsporum canis | 100 |
| Curvularia lunata | >100 |
| Neurospora crassa | >100 |

The MIC (minimum inhibiting concentration) values are obtained in the well known series dilution test. The incubation was effected in a malt extract medium (2%) having a pH of 5.2–5.4 at 27° C. for 48 to 72 hours. The test strains are well known and have been deposited in the fungi collection of the firm Sandoz, Basel, where they are available for examination.

The effect against Candida albicans may be confirmed by in vivo tests, for example in the well known sepsis infection test in the mouse on administration s.c. of from about 2 to about 15 mg/kg/day animal body weight of the compound, according to the principles of H. B. R. Seeliger, Handbuch der experimentalen Pharmacologie XVI/II/A, page 27 et seg.

The compound S 31794/F-1 is therefore useful as an anti-mycotic for combatting *Candida albicans* infections.

For the above use the dosage will, of course, vary depending on the compound employed and therapy desired. However, in general, satisfactory results are obtained with a daily dosage of from about 0.01 to about 300 mg/kg animal body weight per day, and in particular from about 0.01 to about 15 mg/kg for parenteral administration and from about 10 to about 300 mg/kg for enteral administration. For the larger mammal an indicated daily dose is from 20 to 150 mg of the compound for parenteral administration, conveniently administered in divided dosages 2 to 4 times a day in unit dosage form containing about 5 to about 75 mg of the compound, or in sustained release form. As an alternative the compound may be administered orally. The indicated dose is from 1 to 3 g, conveniently administered in divided dosages 2 to 4 times a day in unit dosage form containing from about 250 mg to 1.5 g, or in sustained release form.

The invention also provides a pharmaceutical composition comprising S 31694/F-1 in association with a pharmaceutical carrier or diluent.

Such compositions conveniently contain more than 1% by weight of the active compound and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents, such as methyl cellulose, tragacanth and sodium alginate, wetting agents such as lecithin, polyoxy-ethylene stearate and polyoxyethylene sorbitan monooleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegrating of the tablet and absorption of the active ingredient in the gastro-intestinal tract and thereby provide sustained action over a long period.

The preferred compositions from the standpoint of ease of administration are solid compositions, particularly solid-filled gelatin capsules and tablets.

In the following Examples all temperatures are in degrees Centigrade, and are uncorrected.

All indicated ratios are in parts by volume except when otherwise stated.

Merck is a Trade Mark.

EXAMPLE 1:

Culture of NRRL 8095

10 liters of a nutrient solution containing per liter, 20 g of glucose, 5 g of casein peptone, 3 g of $NaNO_3$, 1 g of $K_2HPO_4$, 0.5 g of KCl, 0.5 g of $MgSO_4 \cdot 7H_2O$, 10 mg of $FeSO_4 \cdot 7H_2O$ and the remainder demineralised water, are inoculated with 1 liter of a pre-culture of the strain NRRL 8095 and incubated for 4 days at 18° in a 10 liter glass fermenter with stirring (150 r.p.m.) and with ventilation (1 l air/min./l nutrient solution).

The pre-culture used as the initial material is obtained as follows:

The spore and mycelium suspension used for inoculation is produced from a culture of the originally isolated strain NRRL 8095, which is cultured for 10 days at 27° on an agar medium containing per liter 20 g of malt extract, 20 g of agar, 4 g of yeast extract and the remainder demineralised water. The spores and the mycelium of this culture are absorbed in a physiological cooking salt solution. With this suspension, 1 liter of a nutrient solution containing per liter 20 g of malt extract, 4 g of yeast extract and the remainder demineralised water is inoculated, and is incubated for 2 days at 27° in a 2 liter Erlenmeyer flask on a circular shaking machine. This culture broth serves as the inoculating material for the 10 liter glass fermenter.

EXAMPLE 2:

Cultivation of NRRL 8095 (alternative method)

A steel fermenter with 50 liters of a medium containing per liter, 200 g Saccharose, 10 g Soya protein, 10 g yeast extract, 10 g malt extract, 2 g $KH_2PO_4$, 2 g $MgSO_4 \cdot 7H_2O$ and the remainder demineralised water are inoculated with 10 liters of a secondary pre-culture. The fermentation proceeded for 12 hours at 24° at pH 5-7, aeration of 0.7-1 liter air/min./liter medium and a increasing stirring rate of 150-400 r.p.m The pre-culture used as starting material is obtained as follows:

The incubation of the strain NRRL 8095 in slanting tubes for the production of conidas is effected for 19 days at 27° in a medium comprising per liter, 100 g Sorbit (hexavalent alcohol from Hexil), 10 g Trypton (a Casein peptone three times digested), 250 g $KH_2PO_4$, 250 mg $MgSO_4 \cdot 7H_2O$, 250 mg $Ca(NO_3)_2 \cdot 4H_2O$, 125 mg KCl, 16 mg $FeSO_4 \cdot 7H_2O$, 7 mg $ZnSO_4 \cdot 7H_2O$, 15 g Agar and the remainder to 1 liter demineralised water.

For the production of a primary pre-culture 1 liter of pre-culture medium (comprising 20 g malt extract and 4 g yeast extract and the remainder to 1 liter demineralised water) in 2 liter Erlenmeyer retorts is inoculated with $8-9 \times 10^9$ conidas in 10 ml 0.9% sodium chloride solution and incubated for 4 days at 24° on a circular shaking machine at 180 r.p.m.

For the production of the secondary pre-culture 2 liters of primary pre-culture in a glass fermentar are incolutated with 10 liters of pre-culture medium and incubated for 4 days at 24°, 150 r.p.m., and aeration of 0.5 liter/min./liter medium.

EXAMPLE 3:

Isolation of S 31794/F-1

90 liters of a culture broth obtained according to Example 1 or 2 is treated with 90 liters of a mixture of ethyl acetate/isopropanol (4:1) and homogenized at room temperature for 30 minutes using an Ultraturrax. The organic phase is separated off with a separator, and evaporated in a vacuum at 40° or less. The evaporation residue is chromatographed on ten-fold amount of silica gel (Merck 0.06-0.2 mm). The crude extract first is taken up on a 1 to 2-fold amound of silica gel (Merck; 0.2-0.5 mm), by using the smallest possible amount of methanol or aqueous methanol. The so-impregnated silica gel is suspended in chloroform:methanol (95:5) and the pulp transferred to the chromatographed column. The eluant used is chloroform:methanol (95:5) initially the with doubling of the methanol amount up to 40%. The fractions are tested for activity against Candida albicans and also by thin layer chromatography.

The active fractions are chromatographed further on 100 times amount of Sephadex LH20 with methanol. The franctions are tested again for their activity and by thin layer chromatography. The antibiotic is further chromatographed on 100 times amount of silica gel (Merck; 0.05-2 mm) using chloroform/methanol/water (71:25:4).

The fractions are screened using thin layer chromatography. The residue obtained on evaporating the active fractions are disolved in methanol and ether is added. S 31794/F-1 is obtained in the form of a white amorphous powder. After drying in a high vacuum S 31794/F-1 melts at 178°-180° (decomposition). For obtaining crystalline S 31794/F-1 a 10 times amount of ethyl acetate/methanol/water (80:12.8) is used yielding thread like crystals; M.Pt. 181°-183° (decomp.) after drying in a high vacuum at 20°.

Figure 1:
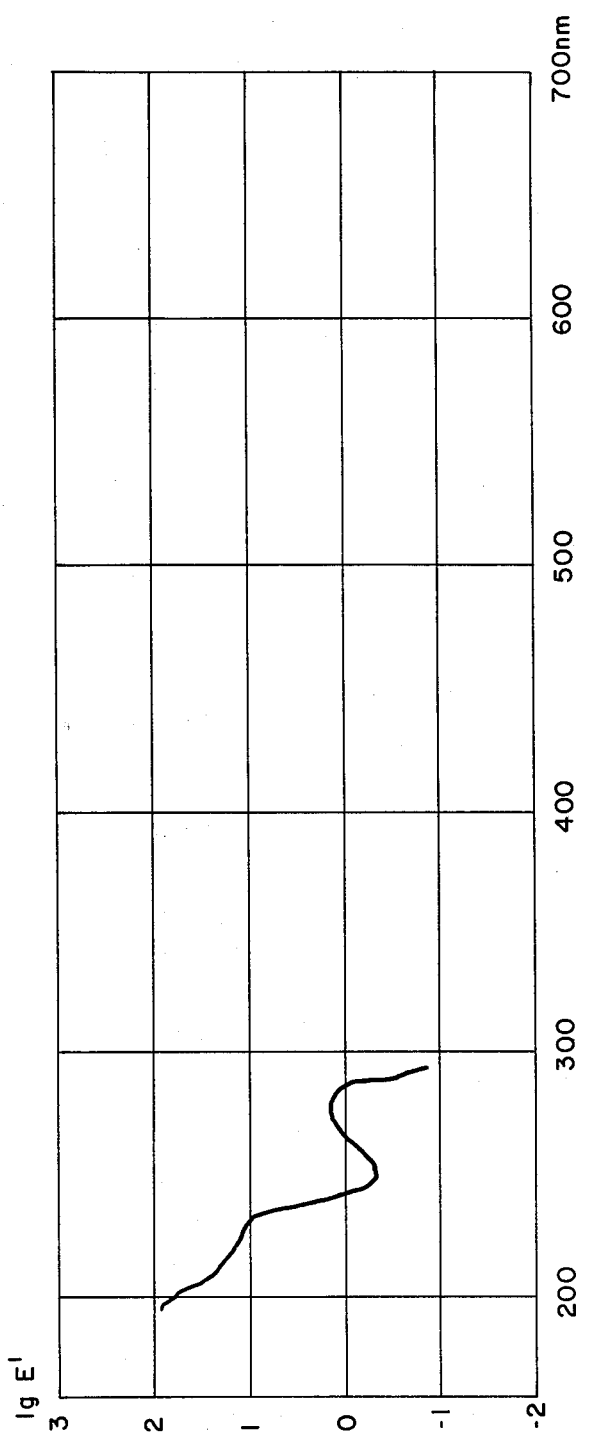

We claim:

1. A compound S 31794/F-1 having the following characteristics:

$\lambda_{MAX}$ 194 nm $E_{1\ cm}^{1\%} = 807$, $\lambda_{MAX}$ 225 nm (shoulder) $E_{1\ cm}^{1\%} = 132$, $\lambda_{MAX}$ 276 nm $E_{1\ cm}^{1\%} = 12.8$, $\lambda_{MAX}$ 284 nm (shoulder) $E_{1\ cm}^{1\%} = 10.5$, (see FIG. 1);

$^1H$ NMR spectrum in deuterated DMSO (100 megacycles per second second) with tetramethylsilane as internal standard (see FIG. 4);

$^{13}C$ NMR spectrum in deuterated methanol ($D_4$) with tetramethylsilane as internal standard (see Table 1);

and having the following additional characteristics in amorphous form;

elementary analysis: C 53.9%, H 7.5%, N 10.1%, O 27.3%; IR spectrum in kBr (see FIG. 2);

and having the following additional characteristics in crystalline form:

elementary analysis: C 55.5–56.5%, H 7.5–7.7%, N 10.5–10.8%, O 26.5–27.0%; IR spectrum in Nujol (see FIG. 3).

2. The compound of claim 1 in amorphous form.

3. The compound of claim 1 in crystalline form.

4. A process for the production of an antibiotic S 31794/F-1 having the following characteristics:

UV spectrum in methanol:

$\lambda_{MAX}$ 194 nm $E_{1\ cm}^{1\%} = 807$, $\lambda_{MAX}$ 225 nm (shoulder) $E_{1\ cm}^{1\%} = 132$, $\lambda_{MAX}$ 276 nm $E_{1\ cm}^{1\%} = 12.8$, $\lambda_{MAX}$ 284 nm (shoulder) $E_{1\ cm}^{1\%} = 10.5$, (see FIG. 1);

$^1$H NMR spectrum in deuterated DMSO (100 megacycles per second second) with tetramethylsilane as internal standard (see FIG. 4);

$^{13}$C NMR spectrum in deuterated methanol (D$_4$) with tetramethylsilane as internal standard (see Table 1); and having the following additional characteristics in amorphous form:

elementary analysis: C 53.9%, H 7.5%, N 10.1%, O 27.3%; IR spectrum in kBr (see FIG. 2);

and having the following additional characteristics in crystalline form;

elementary analysis: C 55.5–56.5%, H 7.5–7.7%, N 10.5–10.8%, O 26.5–27.0%; IR spectrum in Nujol (see FIG. 3);

which comprises cultivating the strain NRRL 8095 of *Acrophialophora limonispora* nov. spec. Dreyfus+-Muller under aerobic fermentation conditions in a nutrient medium until a sufficient amount of antibiotic S 31794/F-1 is produced.

5. A pharmaceutical composition for treating *Candida albicans* comprising a *Canadida albicans* inhibiting effective amount of a compound of claim 1 in association with a pharmaceutical carrier or diluent.

6. A method of combatting *Candida albicans* infections in animals which comprises administering a *Candida albicans* inhibiting effective amount of a compound of claim 1 to an animal in need of such treatment.

* * * * *